United States Patent [19]

Sunshine et al.

[11] Patent Number: 4,479,956
[45] Date of Patent: Oct. 30, 1984

[54] ANALGESIC COMPOSITIONS COMPRISING PROPIRAM AND METHODS OF USING SAME

[75] Inventors: Abraham Sunshine, New York; Eugene M. Laska, Larchmont; Carole E. Siegel, Mamaroneck, all of N.Y.

[73] Assignee: Analgeic Associates, Larchmont, N.Y.

[21] Appl. No.: 488,815

[22] Filed: Apr. 26, 1983

[51] Int. Cl.³ .................. A61K 31/44; A61K 31/52
[52] U.S. Cl. ................................. 424/253; 424/263
[58] Field of Search ............................. 424/253, 263

[56] References Cited

PUBLICATIONS

Chem. Abst. 96 (1982) 149162u.
Merck Index, 9th Ed. (1976), pp. 1014–1015.

*Primary Examiner*—Stanley J. Friedman
*Attorney, Agent, or Firm*—Burns, Doane, Swecker & Mathis

[57] ABSTRACT

Novel analgesic compositions for use in eliciting an improved analgesic response are disclosed. The compositions comprise propiram together with caffeine and/or ibuprofen. When used in combination with propiram, ibuprofen enhances the analgesic response. When used in combination with propiram or in combination with propiram and ibuprofen, caffeine enhances the analgesic response and hastens its onset. The compositions of the invention also provide an unexpectedly long duration of analgesic effect.

16 Claims, No Drawings

ANALGESIC COMPOSITIONS COMPRISING PROPIRAM AND METHODS OF USING SAME

This application is a continuation of application Ser. No. 400,646, filed July 22, 1982, now abandoned.

CROSS-REFERENCE TO RELATED APPLICATIONS

The subject matter of this application is related to that of our patent applications entitled "IMPROVED ANALGESIC AND ANTI-INFLAMMATORY COMPOSITIONS COMPRISING IBUPROFEN AND METHODS OF USING SAME" (Attorney Docket No. 026430-001) and "IMPROVED ANALGESIC AND ANTI-INFLAMMATORY COMPOSITIONS COMPRISING CAFFEINE AND METHODS OF USING SAME" (Attorney Docket No. 026430-003) filed concurrently herewith, both incorporated by reference herein and relied upon.

FIELD OF THE INVENTION

The present invention relates to novel pharmaceutical compositions of matter having analgesic properties, said compositions comprising propiram and caffeine, propiram and ibuprofen, and propiram together with both caffeine and ibuprofen. The invention further relates to methods of improving analgesic responses using said compositions.

BACKGROUND ART

Propiram, or N-(1-methyl-2-piperidinoethyl)-N-2-pyridylpropionamide, is a known oral analgesic which has opiate agonist-antagonist properties. It is generally employed in the form of its fumarate salt, which has the structural formula

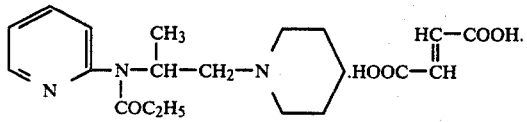

Propiram acts primarily on the central nervous system. Orally, propiram fumarate has been found to be approximately one-twelfth as potent as intramuscular morphine (Saldana, L. R., *Curr. Ther. Res.* 28: 646–649, Nov. 1980) and 1/200 as active as the antagonist morphine. Jasinski (*Br. J. Clin. Pharmacol.* 7: 287A–90S, 1979, supplement) has reported that propiram fumarate seems to have less abuse potential than codeine or propoxyphene. Animal studies have revealed that the analgesic activity is comparable, in terms of effect and duration, to meperidine and codeine. The drug is regarded as less addicting than codeine and as causing less respiratory depression than codeine; it is generally administered orally, in 25 to 50 mg doses, every 4 hours for severe pain, not to exceed 300 mg daily. The most frequently encountered side effect appears to be drowsiness, with nausea, dizziness and psychomimetic effects occurring to a much lesser extent. See also *The Merck Index*, ninth edition, Merck & Co., Inc., Rahway, N.J. (1976), pp. 1014–1015 and the references cited therein.

Ibuprofen, or (±)2-(p-isobutylphenyl)propionic acid, has the structural formula

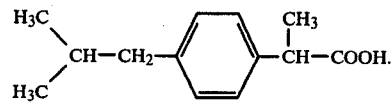

The compound is well-known as a nonsteroidal anti-inflammatory drug having analgesic and antipyretic activity; it is peripherally acting and inhibits prostaglandin synthesis. Ibuprofen is currently marketed in the United States as Motrin ®, which is available in 300, 400 and 600 mg tablets for oral administration. For the treatment of mild to moderate pain, 400 mg every 4 to 6 hours, not to exceed 2400 mg total daily dose, is generally recommended. See also *Physicians' Desk Reference*, 35th edition, 1981, pp. 1831–1833.

Caffeine, or 3,7-dihydro-1,3,7-trimethyl-1H-purine-2,6-dione, has the structural formula

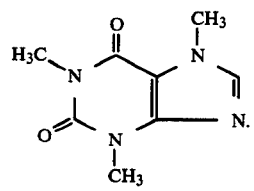

This substance has been used alone, intravenously, in the treatment of headaches and has also been used in combination with selected drugs. Compositions containing one or more of the analgesics aspirin, acetaminophen and phenacetin in combination with varying amounts of caffeine have been marketed in the past; in several cases, such non-narcotic analgesic/caffeine combination products have further included one of the narcotic analgesics codeine, propoxyphene or oxycodone. Examples of these combinations include the products known commercially as Excedrin ®, SK-65 ® Compound, Darvon ® Compound, Anacin ®, A.P.C., and A.P.C. with Codeine, Tabloid ® Brand. The non-steroidal analgesic components of these mixtures have the following structural formulas:

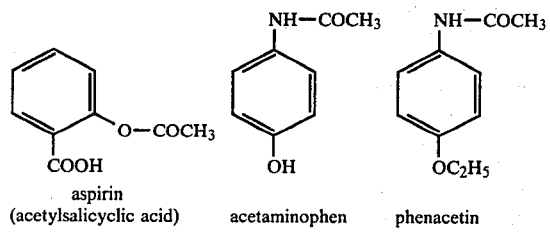

aspirin (acetylsalicyclic acid)    acetaminophen    phenacetin

The three narcotic analgesics which have occasionally been added to the aspirin/phenacetin/acetaminophen/caffeine combinations have the following structural formulas:

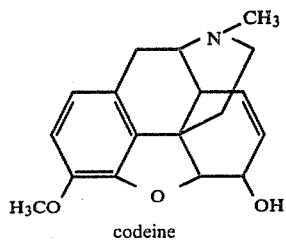
codeine

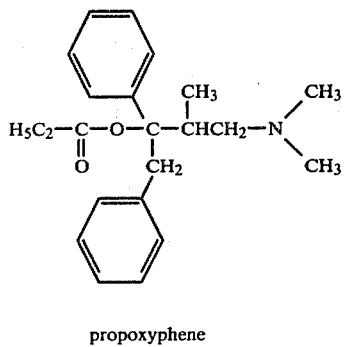
propoxyphene

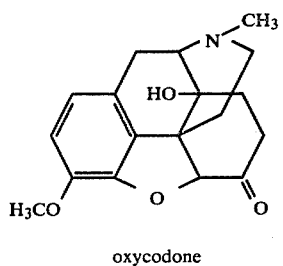
oxycodone

As far as the present inventors know, however, the art has never suggested that caffeine be added to a narcotic analgesic to contribute to its analgesic effect.

Many workers have sought to demonstrate the efficacy of the aspirin/phenacetin/acetaminophen/caffeine combination products. An extensive review of the literature on caffeine and analgesics has been published ["Over-The-Counter Drugs: Establishment of a Monograph for OTC Internal Analgesic, Antipyretic and Antirheumatic Products," *Federal Register*, 1977, 42 (131): 35482-35485] and several relevant additional articles have appeared. Most animal studies on caffeine analgesia have been performed on the rat. Williams (*Toxicology and Applied Pharmacology*, 1959, 1:447-453) utilized experimental pain and found that caffeine alone exerted analgesic effects on rats and when combined with aspirin, the effect appeared additive but not potentiating. Vinegar et al (*Proceedings of the Society for Experimental Biology and Medicine*, 1976, 151:556-560), ten years later, found that in the rat caffeine potentiates the acute anti-inflammatory and analgesic activity of aspirin. Siegers (*Pharmacology*, 1973, 10:19-27) studied the effect of oral doses of caffeine (10, 50 and 100 mg/kg) given to rats together with acetaminophen and found that caffeine inhibited its absorption and lowered its serum concentration. He suggested that delayed stomach emptying as a result of the relaxing effect of caffeine on gastric smooth muscle was probably the cause of the diminished absorption of orally administered drugs in the presence of caffeine. Despite this finding, acetaminophen analgesia was not decreased by caffeine. In agreement with Williams and Vinegar and his associates, Siegers found that caffeine itself had analgesic activity. Only in the lowest dose of caffeine studied, a dose at which analgesia was not exhibited, was there a reduction in the acetaminophen induced analgesia. In a more recent paper, Seegers et al (*Arch. Int. Pharmacodyn.*, 1981, 251:237-254) demonstrated an anti-inflammatory, analgesic effect of caffeine in rats. He also found that the combination of caffeine, aspirin and acetaminophen as well as the combination of caffeine, aspirin and phenacetin at low doses produced anti-inflammatory, analgesic effects which are at least as great as would be expected on the basis of addition, while at high doses, the results suggested potentiation. Citing the work of Giertz and Jurna (*Naturwissenschaften*, 1957, 44:445) and Fuchs and Giertz (*Arzneimittelforsch*, 1960, 10:526-530), who observed that caffeine induced analgesia in assays in mice in which inflammation was not involved, Seegers asserted that, "it seems safe to assume that the analgesic activity of caffeine consists of at least two components, one independent of and another one dependent on its anti-inflammatory activity."

The earliest relevant study in humans was reported by Wallenstein (*Proceedings of the aspirin symposium*, held at the Royal College of Surgeons, London, 1975). Two tablets of a combination in which each tablet contained aspirin 210 mg, acetaminophen 150 mg and caffeine 30 mg, clearly and significantly produced more analgesia than the combination without caffeine. The one tablet dose of the combination had higher mean scores than either component alone, but was not superior to the combination without caffeine. Wallenstein speculated that, "dosage may be an important factor, and caffeine may simply be ineffective much below the 60 mg dose". Booy (*Nederlands Tijdschrift Voor Tandheelkinde*, 1972, 79: 69-75) studied pain relief on each of two days after tooth extraction. Patients who reported "great pain" on the first day obtained more pain relief from 1000 mg of acetaminophen plus 100 mg of caffiene than from 1000 mg of acetaminophen alone. On the second day this difference was not found, although on both days all treatments were superior to placebo. Lim et al (*Clin. Pharmacol. Ther.*, 1967, 8: 521-542) reporting a study in which experimental pain was induced in the subjects by bradykinin, observed that the combination of aspirin 520 mg and acetaminophen 260 mg given orally could not be distinguished from placebo, whereas the same combination in lesser quantities, aspirin 325 mg and acetaminophen 162.5 mg plus caffeine 32.5 mg was significantly different from placebo at 15, 60, 75, 105 and 120 minutes after taking the drug. A double-blind, crossover study of 216 patients by Wojcicki et al [*Archivum Immunologiae et Therapeae Experimentalis*, 1977, 25(2): 175-179] compared the activity of 1000 mg of acetaminophen plus 100 mg of caffeine against the same quantity of acetaminophen alone. One group of patients in the trial were suffering severe and frequently occurring idiopathic headache and a second group had moderate post-operative orthopedic pain. The authors concluded that the relief of pain was far greater with the caffeine combination than with acetaminophen alone or with aspirin alone. Jain et al (*Clin. Pharmacol. Ther.*, 1978, 24: 69-75) first studied 70 postpartum patients with moderate to severe uterine cramp and/or episiotomy pain and then a second group of 70 patients limited to severe pain only. Comparing 800 mg aspirin plus 65 mg of caffeine to 650 mg of aspirin alone, these authors concluded that in patients with severe episiotomy pain the combination is the more effective analgesic.

Caffeine use in the treatment of headache has a long history. The FDA Advisory Panel, in its review of caffeine [*Federal Register,* 1977, 42(131): 35482-35485] argued that the known biochemical effect of caffeine on small blood vessels provides a plausible explanation for its effectiveness in treating headache associated with cerebral blood vessels. Recently Sechzer [*Curr. Therapy Research,* 1979, 26(4)] found that the intravenous administration of caffeine sodium benzoate rapidly provided relief in the majority of patients experiencing headache resulting from dural puncture or spinal anesthesia. The author, referring to the literature on the mechanism of action of caffeine on cerebral blood flow and on cerebral vascular tone, argues from the opposite perspective of the Panel that the analgesic relief obtained implies that an intracranial vascular component is the primary factory in such headaches.

Changes in mood and over all sense of "well being" after administration of caffeine have been widely reported in the literature. Beginning in the early part of this century, Hollingsworth (*Arch. Psychol.,* 1912, 22: 1) reported beneficial motor and mental effects from 65 to 130 mg of caffeine, and tremor, poor motor performance, and insomnia caused by 390 mg of caffeine. Many studies over the past 70 years have confirmed these findings. Review articles on the xanthines [Ritchie, J. M., "Central nervous system stimulants. 2. The xanthines," Goodman, L. S. & Gilman, A. (Eds.) *The pharmacological basis of therapeutics,* 4th Ed., New York: Macmillian Co., 1970; Stephenson, P. E., "Physiologic and psychotropic effects of caffeine on man," *J. Amer. Diet. Assoc.,* 1977, 71(3): 240-247] report that doses of 50 to 200 mg of caffeine result in increased alertness, decreased drowsiness, and lessened fatigue. Doses in the range of 200 to 500 mg may produce headaches, tremor, nervousness and irritability.

After extensively reviewing the relevant literature, the most significant contributions of which are summarized above, the FDA Advisory Panel in 1977 concluded that caffeine when used as an analgesic adjuvant was safe, but that there was insufficient data to demonstrate that caffeine contributes anything to the action of the analgesic [*Federal Register,* 1977, 42(131): 35482-35485]. The Panel stated:

Unfortunately, the information and data submitted, fail to demonstrate conclusively that caffeine in combination is effective as an analgesic, antipyretic and/or antirheumatic ingredient. The Panel finds there is little evidence to show that this ingredient even contributes to these pharmacological effects in the clinical situation.

This remains the official position on the question up to the present time. Consequently, many of the analgesic/caffeine combination products previously available are no longer on the market.

In addition to the few prior art instances of selected non-narcotic analgesic/caffeine combinations further containing a selected narcotic analgesic (which three-component combinations have already been discussed hereinabove), there also are examples in the art of two-component combinations of selected non-narcotic analgesics with selected narcotic analgesics. Known combinations of this type include Darvon ® with A.S.A. ® (propoxyphene hydrochloride and aspirin), Darvon-N ® with A.S.A. ® (propoxyphene napsylate and aspirin), aspirin with codeine, Talwin ® Compound (pentazocine hydrochloride and aspirin), Percodan ® (oxycodone hydrochloride, oxycodone terephthalate and aspirin) and nalbuphine with acetaminophen, the last-mentioned combination being disclosed in U.S. Pat. No. 4,237,140. The general principle of use of a combination of drugs to produce additive analgesic effects is known to those skilled in the art; for example, Foley et al, *The Management of Cancer Pain, Volume II-The Rational Use of Analgesics in the Management of Cancer Pain,* Hoffman-LaRoche Inc., 1981, suggest such combination and specifically point out that 650 mg aspirin of acetaminophen regularly added to the standard narcotic dose will often enhance the analgesic effect without requiring higher doses of the narcotic. Such additive effects have been reported earlier by Houde et al, *Clin. Pharm. Ther.* 1(2): 163-174 (1960) for intramuscularly administered morphine sulfate given with orally administered aspirin. As far as the present inventors know, however, the art does not suggest any two-component compositions of a narcotic analgesic and caffeine; it also does not suggest any improvements in the analgesic response to be derived from co-administering caffeine with any narcotic analgesic.

SUMMARY OF THE INVENTION

Surprisingly, the present inventors now find that propiram can be advantageously combined with caffeine and/or ibuprofen to form novel pharmaceutical compositions which can be administered to mammals, especially humans, to elicit an improved analgesic response.

In one aspect, the present invention thus provides a novel pharmaceutical composition of matter for use in eliciting an analgesic response, said composition comprising an analgesically effective amount of propiram and an amount of caffeine sufficient to enhance analgesia or to hasten its onset.

In another aspect, the present invention provides a novel pharmaceutical composition of matter for use in eliciting an analgesic response, said composition comprising an analgesically effective amount of propiram and an amount of ibuprofen sufficient to enhance analgesia.

In another aspect, the present invention provides a novel pharmaceutical composition of matter for use in eliciting an analgesic response, said composition comprising an analgesically effective amount of propiram, an amount of ibuprofen sufficient to enhance analgesia, and an amount of caffeine sufficient to further enhance analgesia or to hasten its onset.

Typically, the active ingredients in the compositions of the present invention are further associated with a nontoxic pharmaceutically acceptable inert carrier therefor.

The present invention further provides a method of hastening the onset of analgesia in a mammal resulting from administration of an analgesically effective amount of propiram (optionally combined with an analgesia-enhancing amount of ibuprofen), said method comprising administering to said mammal said analgesically effective amount of propiram (optionally combined with an analgesia-enhancing amount of ibuprofen) together with an amount of caffeine sufficient to hasten the onset of analgesia.

The invention further provides a method of eliciting an enhanced analgesic response to a mammal, said method comprising administering to said mammal an analgesically effective amount of propiram together with an amount of caffeine sufficient to enhance the analgesic response, or together with an amount of ibuprofen sufficient to enhance the analgesic response, or together with an amount of ibuprofen sufficient to enhance the analgesic response and an amount of caffeine sufficient to further enhance the analgesic response or to hasten its onset.

DETAILED DESCRIPTION OF THE INVENTION

The term "caffeine" as used herein is intended to encompass not only caffeine as the anhydrous powder, but any salt or derivative of caffeine or any compounded mixture thereof which is non-toxic, pharmaceutically acceptable and which is capable of hastening or enhancing an analgesic response when combined with propiram. See, for example, *The Merck Index*, ninth edition, Merck & Co., Rahway, N.J. (1976), pp. 207-208, for a description of such salts, derivatives and mixtures which may prove useful in the compositions of the present invention. Nevertheless, caffeine as the anhydrous powder base is presently preferred and, where specific amounts of caffeine are set forth below, such amounts are given in mg of the anhydrous base.

The term "ibuprofen" as used herein is intended to encompass not only 2-(p-isobutylphenyl)propionic acid itself but also any pharmaceutically acceptable salt thereof, e.g. ibuprofen aluminum (*Chemical Abstracts* Registry No. 61054-06-6). However, where specific amounts of ibuprofen are set forth below, such amounts are given in mg of the acid unless otherwise specified.

The term "propiram" as used herein is intended to encompass not only the preferred fumarate salt, N-(1-methyl-2-piperidinoethyl)-N-2-pyridiylpropionamide fumarate, but any pharmaceutically acceptable form, e.g. salt, of the free base which is similarly active pharmacologically. However, where specific amounts of drug are set forth below, such amounts are given in mg of propiram furmarate, the preferred form, unless otherwise specified. Corresponding amounts of free base can be calculated using the following conversion factors:

100 mg propiram fumarate = 70.33 propiram base
100 mg propiram base = 142.18 mg propiram fumarate.

Corresponding amounts of other salts can be calculated in similar manner.

Propiram, when combined with caffeine in accord with the present invention, produces the following unexpected results:

(1) the analgesic effect of propiram on the mammal is brought on more quickly;
(2) lower amounts of propiram are required for the same analgesic effect; and
(3) across all doses, a greater analgesic response is achieved.

For the patients suffering pain, the time from administration of medication to the onset of effective relief is clearly of paramount importance. The present inventors' discovery that caffeine substantially shortens the onset time (i.e. substantially hastens the onset) of analgesia is therefore very significant; moreover, it is completely unexpected.

Further, the ability of caffeine to enhance analgesia, i.e. to substantially reduce the amount of propiram which is required to elicit a given analgesic response, is also an unexpected and very important aspect of this invention. This unexpected and important finding permits the use of propiram in quantities substantially less than the dosages presently suggested as an analgesic agent in humans. Use of lower doses should in turn lower the incidence and/or severity of undesirable side effects, including lessening addiction potential. Moreover, at a given dosage level, a greater analgesic response can be achieved.

More specifically, it is believed that onset time for analgesia can be reached, on the average, about one-fourth to about one-third sooner when a propiram/caffeine composition of the invention is used rather than when propiram alone is employed. Also, approximately one-fifth to one-third less propiram can be used in the caffeine combination to achieve the same analgesic effect as that obtained by use of propiram alone; in other words, the addition of caffeine decreases the amount of propiram needed to two-thirds to four-fifths of the usual amount to achieve the same effect. These ratios may vary, however, depending on the patient's individual response, the selected dosage level of the active ingredients etc.

The propiram/caffeine composition of the present invention possesses significant advantages additional to those outlined above. Thus, the present inventors believe that the composition may have a longer duration of action than previously known for propiram alone, effective levels of analgesia being seen for 6 hours after administration. In view of this, the drug may need be administered only 4 times daily rather than every 4 hours, which further reduces the patient's daily intake of propiram and may further reduce side-effects and dependence liability. Moreover, the use of caffeine counteracts the sedative effects of propiram such that the patient is more alert, has better motor skills and may have an improved sense of well-being as compared to when propiram is administered alone.

The precise amount of propiram for use in the present propiram/caffeine compositions will vary depending, for example, on the size and kind of the mammal and the condition for which the drug is administered. For use in humans, the analgesically effective amount of propiram in a unit dose composition will typically be from about 25 to 60 mg (as the fumarate). The amount of caffeine in the analgesic composition will be an amount sufficient to shorten the onset time and/or to enhance analgesia. For humans, a unit dosage analgesic composition will typically contain from about 60 to about 250 mg caffeine; this dosage level of caffeine is generally sufficient to both shorten the onset time and enhance analgesia. The daily analgesic dose in humans generally will not exceed 300 mg (preferably 240 mg) propiram fumarate and 1000 mg caffeine, although greater amounts could be employed if tolerated by the patient.

Preferred propiram/caffeine unit dosage compositions for use in the treatment of moderate to severe pain include about 35 to 50 mg propiram fumarate plus about 65 to 150 mg caffeine.

Propiram, when combined with ibuprofen in accord with the present invention, provides enhanced analgesia; at a given dosage level, the analgesic effect of the combination is greater than for either propiram or ibuprofen alone. Consequently, it is possible to lower the amount of propiram administered, if desired, and achieve the same level of analgesia as with a higher dose of propiram alone. This lowering of dosage should lead to lower incidence and less severity of side effects, and less likelihood of addiction potential. Moreover, propiram plus ibuprofen may provide a longer duration of action than is known for either propiram or ibuprofen alone; effective levels of analgesia could then be obtained for 6 hours after administration. The drugs therefore would need to be administered only 4 times daily rather than every 4 hours, which further reduces the patient's daily intake of propiram and may further reduce side-effects and dependence liability. Also, because of the expected longer duration of activity and the sedative properties of propiram, the propiram/ibuprofen combination is an exceptionally good night-time analgesic which should enable even the patient suffering from severe pain to obtain needed rest and sleep.

More specifically regarding the propiram/ibuprofen composition of the invention, approximately one-fifth to one-third less propiram can be used in the combination to achieve the same analgesic effect as that obtained by use of propiram alone; in other words, the addition of ibuprofen decreases the amount of propiram needed to two-thirds to four-fifths of the usual amount to achieve the same effect. These ratios may vary, however, depending on the patient's individual response, the selected dosage level of the active ingredients etc.

The precise amount of propiram for use in the propiram/ibuprofen compositions will vary depending, for example, on the size and kind of the mammal and the condition for which the drug is administered. For use in humans, the analgesically effective amount of propiram in a unit dose composition will typically be from about 25 to 60 mg, preferably about 35 mg (as the fumarate). The amount of ibuprofen in the analgesic composition will be an amount sufficient to enhance analgesia. For humans, a unit dosage analgesic composition will typically contain from about 100-400 mg ibuprofen, preferably 200-400 mg ibuprofen; this dosage level of ibuprofen is an amount well tolerated alone when used to treat mild to moderate pain and is sufficient to enhance analgesia when combined with propiram. The daily analgesic dose in humans generally will not exceed 300 mg (preferably 240 mg) propiram fumarate and 2400 mg (preferably 1600 mg) ibuprofen, although greater amounts could be employed if tolerated by the patient. Preferred propiram/ibuprofen unit dosage compositions for use in the treatment of moderate to severe pain include about 35 mg propiram fumarate and about 200 to 400 mg ibuprofen.

Propiram, when combined with caffeine and ibuprofen in accord with the present invention, produces all of the unexpected results and has all of the advantages discussed in detail above for the propiram/caffeine combination. Moreover, the propiram/ibuprofen/caffeine combination shares all of the characteristics and advantages of the propiram/ibuprofen combination, except that the presence of caffeine counteracts the sedative properties of propiram. The propiram/ibuprofen/caffeine combination is especially of interest as a daytime oral analgesic, effective against severe pain, which can be utilized in patients who must remain alert and active.

It is believed that caffeine enhances the analgesic effect not only of propiram but also of ibuprofen in the three-component combination; and that caffeine enhances the onset of analgesia from both of these drugs. This is likely to produce a stronger analgesic response than that produced, not only by propiram alone or ibuprofen alone, but also by the propiram/caffeine and propiram/ibuprofen combinations of the invention. Nevertheless, it is not generally recommended that the amounts of propiram and ibuprofen in the propiram/ibuprofen/caffeine composition be further reduced from those utilized in the propiram/ibuprofen combination; rather, the three-component composition is intended to take advantage of the further enhanced and quicker analgesia provided by the presence of caffeine. Thus, for use in treating humans, the analgesically effective amount of propiram in a unit dose three-component composition will typically be from about 25 to 60 mg, preferably about 35 mg (as the fumarate); the amount of ibuprofen in said composition sufficient to enhance analgesia will be from about 100-400 mg (preferably 200-400 mg); and the amount of caffeine in said composition sufficient to further enhance analgesia or to hasten its onset will be from about 60 to 250 mg. The daily analgesic dose in humans will generally not exceed 300 mg (preferably 240 mg) propiram fumarate, 2400 mg (preferably 1600 mg) ibuprofen and 1000 mg caffeine. Preferred propiram/ibuprofen/caffeine unit dosage compositions for use in the treatment of moderate to severe pain include about 35 mg propiram fumarate, about 200 to 400 mg ibuprofen and about 65 to 150 mg caffeine.

While the compositions of the invention are preferably for oral use, they may also be formulated for and administered by other methods which are known for administering analgesics, e.g. as suppositories. Also, the preferred human dosage levels indicated above are for use in adults; if used in pediatrics, the compositions would contain proportionately less of the active ingredients.

The compositions of the present invention are very conveniently administered to mammals by any route of administration suitable for propiram (and ibuprofen, if present), e.g. oral or rectal. Preferably, the combination is formulated with any suitable nontoxic pharmaceutically acceptable inert carrier material. Such carrier materials are well known to those skilled in the art of pharmaceutical formulations. For those not skilled in the art, reference is made to the text entitled, "REMINGTON'S PHARMACEUTICAL SCIENCES" (Fourteenth Edition), 1970. In a typical preparation for oral administration, e.g., tablet or capsule, propiram in an analgesically effective amount and caffeine and/or ibuprofen in the amounts indicated hereinabove are combined with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citris pulp, carboxymethylcellulose and sodium lauryl sulfate. If desired, a conventional pharmaceutically acceptable dye can be incorporated into the dosage unit form, i.e., any one of the standard FD&C dyes. Sweetening and flavoring agents and preservatives can also be included, particularly when a liquid dosage form is formulated, e.g. an elixir, suspension or syrup. Also, when the dosage form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. Such compositions should preferably contain at least 0.1% of active components; generally, the active ingredients will be between about 2% to about 60% of the weight of the unit. Typical unit dosage forms for oral administration will contain 25 to 60 mg propiram and 100 to 400 mg ibuprofen and/or 60 to 250 mg caffeine. Illustrative of typical unit dosage forms are tablets or capsules containing 35 mg propiram+65 or 130 mg caffeine; 50 mg propiram+130 mg caffeine; 35 mg propiram+200 mg ibuprofen; 35 mg propiram+400 mg ibuprofen; 35 mg propiram+200 mg ibuprofen+65 or 130 mg caffeine; and 35 mg propiram+400 mg ibuprofen+65 or 130 mg caffeine.

The above examples are typical when all active ingredients are formulated for immediate release. If one or more of the active components is/are formulated for sustained release, much larger amounts would of course be incorporated in an individual dosage unit.

If desired, compositions of the present invention may be formulated for parenteral use by known methods. The two-component propiram/caffeine parenteral composition should be of particular value in the case of patients suffering severe pain who cannot tolerate such medication administered orally.

It is also possible to formulate the oral compositions of the invention in such a manner that the possibility that propiram could be extracted therefrom and then abused parenterally will be significantly reduced. This may be accomplished by combining the drugs with methylcellulose to form a dosage form that is insoluble in water. Such a methylcellulose-containing tablet is already known for propiram alone.

The analgesic effects of the compositions of the present invention can be quantitatively evaluated in animals in the tests described below:

Antiphenylquinone Writhing Test

This test is a standard procedure for detecting and comparing analgesic activity and generally correlates well with human efficacy.

Mice are first dosed with the medications studied. The medications used are two dose levels of propiram with and without caffeine and two dose levels of propiram+ibuprofen with and without caffeine. The mice are then challenged with phenyl-p-benzoquinone given intraperitoneally and observed for the characteristic stretch-writhing syndrome. Lack of writhing constitutes a positive response. The degree of analgesic protection can be calculated on the basis of suppression of writhing relative to control animals run the same day. Time response data are also obtained. The test is a modification from the methods of Sigmund et al and Blumberg et al (Sigmund, E., Cadmus, R., and Lu, G., *Proc. Soc. Exp. Biol. and Med.* 95, 729-731, 1957; Blumberg, H. et al, *Proc. Soc. Exp. Biol. Med.* 118, 763-766, 1965).

The Mouse Tail-flick Test

Tail-flick testing in mice is modified after D'Amour and Smith, using controlled high intensity heat applied to the tail. Normal and drug-treated mice are observed and the reaction time is measured. The drugs used are two doses of propiram with and without caffeine. (D'Amour, E., and Smith, L., *J. Pharmacol.*, 72, 74-79, 1941).

Haffner Tail-pinch Method

A modification of the procedure of Haffner is used to ascertain drug effects on the aggressive attacking responses elicited by a pressure stimulus pinching the tail of a rat. A clamp is on the base of each rat's tail prior to drug treatment and again at specified intervals after treatment. The time required to elicit clear attacking and biting behavior directed towards the stimulus is observed. The medications studied are two doses of propiram with and without caffeine. (Haffner, F.: *Experimentelle Prufung Schmerzstillender Mittel. Deutsch med. Wschr.*, 55, 731-732, 1929).

Mouse Hot-Plate Test (Thermal Stimuli)

A modification of the method of Woolfe and MacDonald is used and involves the application of a controlled heat stimulus to the paws of mice. Drug is administered to the treatment group. The latency between the time of the animal's contact with the hot-plate and the observation of the standard pain response, jumping and/or rapid patting of one or both hind paws, is measured. The medications studied are two doses of propiram with and without caffeine. (Woolfe, G., and MacDonald, A. D.: *J. Pharmacol. Exp. Ther.*, 80, 300-307, 1944).

To establish the efficacy of the compositions of this invention in humans, patients with moderate to severe pain requiring an oral analgesic can be administered propiram with and without caffeine and propiram+ibuprofen, with and without caffeine. A nurse observer interviews the patients as to their level of pain at subsequent periods of time. Patients are asked to subjectively estimate the time at which the medication begins to provides relief. Appropriate statistical methods can be used to show that on the average the analgesics with caffeine have the shorter onset and are more efficacious. (Laska, E., Gormerly, M., Sunshine, A., Belleville, J. W., Kantor, T., Forrest, W. H., Siegel, C., and Meisner, M.: "A Bioassay Computer Program for Analgesic Clinical Trials", *Clin. Pharmacol. Ther.* 8: 658, 1967; Cox, D. R., "Regression Models and Life Tables", *Journal Royal Statistical Society*, Series B, Volume 34: 187-202, 1972).

From the foregoing description, one of ordinary skill in the art can easily ascertain the essential characteristics of the instant invention, and without departing from the spirit and scope thereof, can make various changes and/or modifications of the invention to adapt it to various usages and conditions. As such, these changes and/or modifications are properly, equitably and intended to be, within the full range of equivalence of the following claims.

What we claim is:

1. A pharmaceutical composition of matter for use in eliciting an analgesic response in a mammal, said composition comprising an analgesically effective amount of propiram and an amount of caffeine sufficient to hasten the onset of the analgesic response.

2. A pharmaceutical composition of matter for use in eliciting an analgesic response in a mammal, said composition comprising an analgesically effective amount of propiram and an amount of caffeine sufficient to enhance the analgesic response.

3. A composition according to claim 1 or 2, comprising from about 25 to about 60 mg propiram fumarate.

4. A composition according to claim 1, comprising from about 60 to about 250 mg caffeine.

5. A composition according to claim 4, comprising from about 25 to about 60 mg propiram fumarate.

6. A composition according to claim 5, comprising from about 35 to about 50 mg propiram fumarate and from about 65 to about 150 mg caffeine.

7. A composition according to claim 1, further comprising a nontoxic pharmaceutically acceptable inert carrier.

8. A composition according to claim 7, said composition being adapted for oral administration.

9. A composition according to claim 8, said composition being formulated as a tablet or capsule.

10. A composition according to claim 7, said composition being adapted for rectal administration.

11. A composition according to claim 10, said composition being formulated as a suppository.

12. A method for hastening the onset of analgesia in a mammal resulting from administration of an analgesically effective amount of propiram, said method comprising administering to said mammal said analgesically effective amount of propiram together with an amount of caffeine sufficient to hasten the onset of analgesia.

13. A method for eliciting an enhanced analgesic response in a mammal, said method comprising administering to said mammal an analgesically effective amount of propiram together with an amount of caffeine sufficient to enhance the analgesic response.

14. A method according to claim 12, wherein the mammal is a human being.

15. A method according to claim 14, comprising administering from about 25 to about 60 mg propiram fumarate together with from about 60 to about 250 mg caffeine.

16. A method according to claim 14, comprising administering from about 35 to about 50 mg propiram fumarate together with from about 65 to about 150 mg caffeine.

* * * * *